US00PP27238P3

(12) United States Plant Patent
Danziger

(10) Patent No.: US PP27,238 P3
(45) Date of Patent: Oct. 4, 2016

(54) ***PETUNIA* PLANT NAMED 'DCAS301'**

(50) Latin Name: *Petunia sensu wijsman*
Varietal Denomination: DCAS301

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 94 days.

(21) Appl. No.: 14/121,493

(22) Filed: Sep. 10, 2014

(65) Prior Publication Data

US 2016/0073569 P1 Mar. 10, 2016

(51) Int. Cl.
*A01H 5/02* (2006.01)

(52) U.S. Cl.
USPC ..... Plt./356.13

(58) Field of Classification Search
USPC ..... Plt./256.13, 356.21, 356.18, 356.13
See application file for complete search history.

(56) References Cited

PUBLICATIONS

Plants with Restricted Propagation May 2014, retrieved on Feb. 3, 2016, retrieved from the Internet at <http://02d788f.netsolhost.com/pdfs_2014/Restricteds_2014_May.pdf> 10 pages.*
Schenck Spring Plants, retrieved on Feb. 3, 2016, retrieved from the Internet at <http://jvk.net/wp/wp-content/uploads/2013/12/Schenck-spring-plants-brochureR.pdf> pp. 1-11.*

* cited by examiner

*Primary Examiner* — June Hwu
(74) *Attorney, Agent, or Firm* — Cassandra Bright

(57) ABSTRACT

A new and distinct *Petunia* cultivar named 'DCAS301' is disclosed, characterized by abundant medium sized flowers, unique red-purple with white rim flower coloration, strong plant vigor and a very well branched semi-trailing plant form. The new variety is a *Petunia,* normally produced as an outdoor garden or container plant.

2 Drawing Sheets

Figure 1:
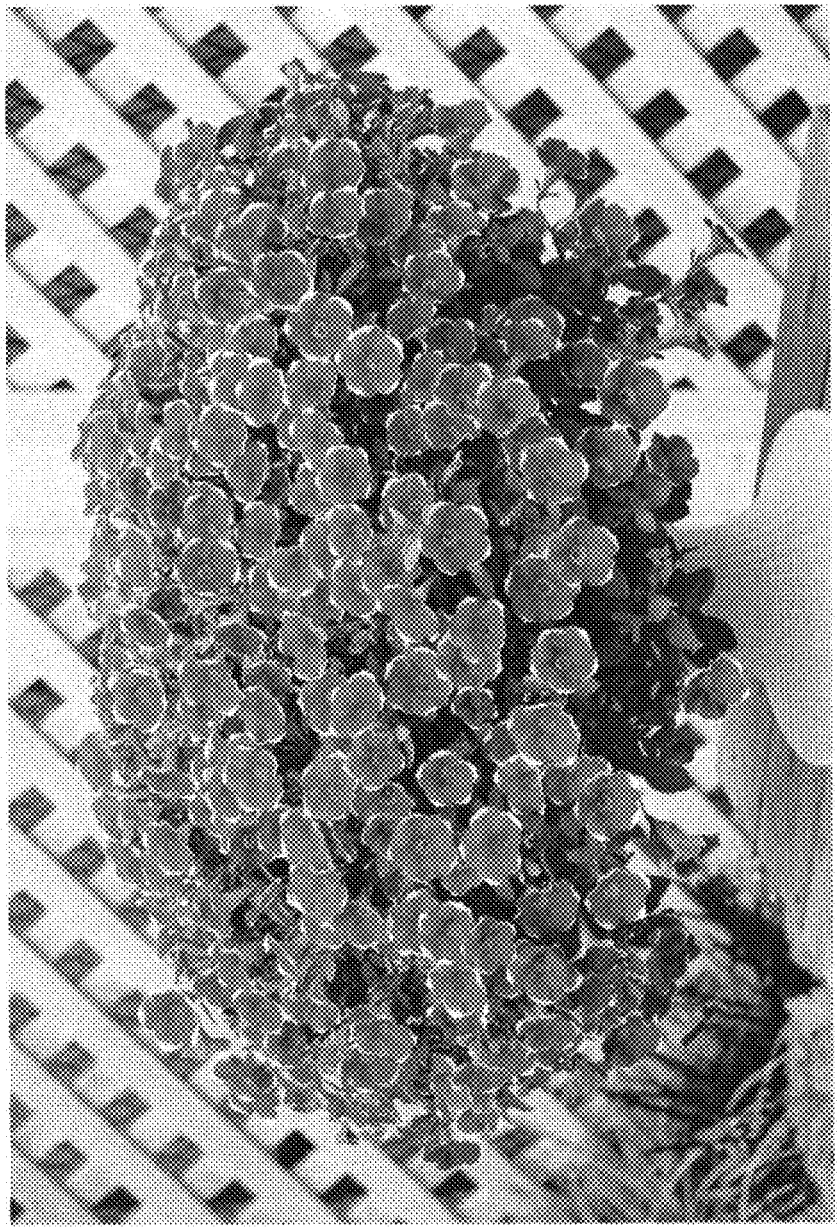

Latin name of the genus and species: *Petunia sensu wijsman.*

Variety denomination: 'DCAS301'.

BACKGROUND OF THE INVENTION

The new *Petunia* cultivar is a product of a planned breeding program conducted by the inventor, Gavriel Danziger, in Moshav Mishmar Hashiva, Israel. The objective of the breeding program was to produce new *Petunia* varieties for ornamental commercial applications. The cross resulting in this new variety was made during September of 2006.

The seed parent is the unpatented, proprietary variety referred to as *Petunia sensu wijsman* 'cv. 6-921'. The pollen parent is the unpatented, proprietary variety referred to as *Petunia sensu wijsman* 'cv. 6-1028'. The new variety was discovered in May of 2007 by the inventor in a group of seedlings resulting from the 2006 crossing, in a research greenhouse in Moshav Mishmar Hashiva, Israel.

Asexual reproduction of the new cultivar was performed by terminal vegetative cuttings. This was first performed at a research greenhouse in Moshav Mishmar Hashiva, Israel in June of 2007 and has shown that the unique features of this cultivar are stable and reproduced true to type in more than 25 successive generations.

SUMMARY OF THE INVENTION

The cultivar 'DCAS301' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCAS301' These characteristics in combination distinguish 'DCAS301' as a new and distinct *Petunia* cultivar:

1. Semi-trailing growth habit.
2. Well branched plant with strong vigor.
3. Flowers color is red-purple with a white rim.
4. Flower size is medium.
5. Abundant flowering.

Plants of the new cultivar 'DCAS301' are similar to plants of the seed parent, in most horticultural characteristics, however, plants of the new cultivar 'DCAS301' differ in the following:

1. Semi-trailing growth habit compared to the trailing growth habit of the seed parent.
2. Greater plant vigor.
3. Flowers color is red-purple with a white rim; seed parent flower color is pink with white stripes.
4. Smaller flower size.
5. Greater quantity of flowers.

Plants of the new cultivar 'DCAS301' are similar to plants of the pollen parent; in most horticultural characteristics, however, plants of the new cultivar 'DCAS301' differ in the following;

1. Semi-trailing growth habit compared to the semi upright growth habit of pollen parent.
2. Very well branched plant compared to the moderately well branched form of the pollen parent.

3. Flowers color is red-purple with a white rim; pollen parent flower color is red with white rim.
4. Larger flower size.
5. Greater quantity of flowers.

COMMERCIAL COMPARISON

Plants of the new cultivar 'DCAS301' are comparable to the commercial variety *Petunia* 'Danlitt240' unpatented. The two *Petunia* varieties are similar in most horticultural characteristics; however, the new variety 'DCAS301' differs in the following:

1. Comparator flower size is smaller than the flower of the new variety
2. Flower color is Purple with White stripes, while the new variety has Red-Purple flowers with a white rim.
3. Comparator plant has a mounded growth habit, while the new variety has a semi-trailing growth habit.
4. Comparator plant is compact, while the new variety has a strong vigor.

Plants of the new cultivar 'DCAS301' can also be compared to the commercial variety *Petunia* 'DANRAY3', unpatented. These varieties are similar in most horticultural characteristics; however 'DCAS301' differs in the following:

1. Comparator flower size is larger than the flower of the new variety.
2. Comparator flower color is Light Purple with dark Purple veins, while the new variety has Red-Purple flowers with a White Rim.
3. Comparator plant has a mounded growth habit, while the new variety has a semi-trailing growth habit.

BRIEF DESCRIPTION OF THE PHOTOGRAPHS

The accompanying photograph in FIG. 1 illustrates in full color a typical plant of 'DCAS301' grown in a greenhouse, in a 13 cm pot. Age of the plant photographed is approximately 3 months from a rooted cutting.

Figure 2:
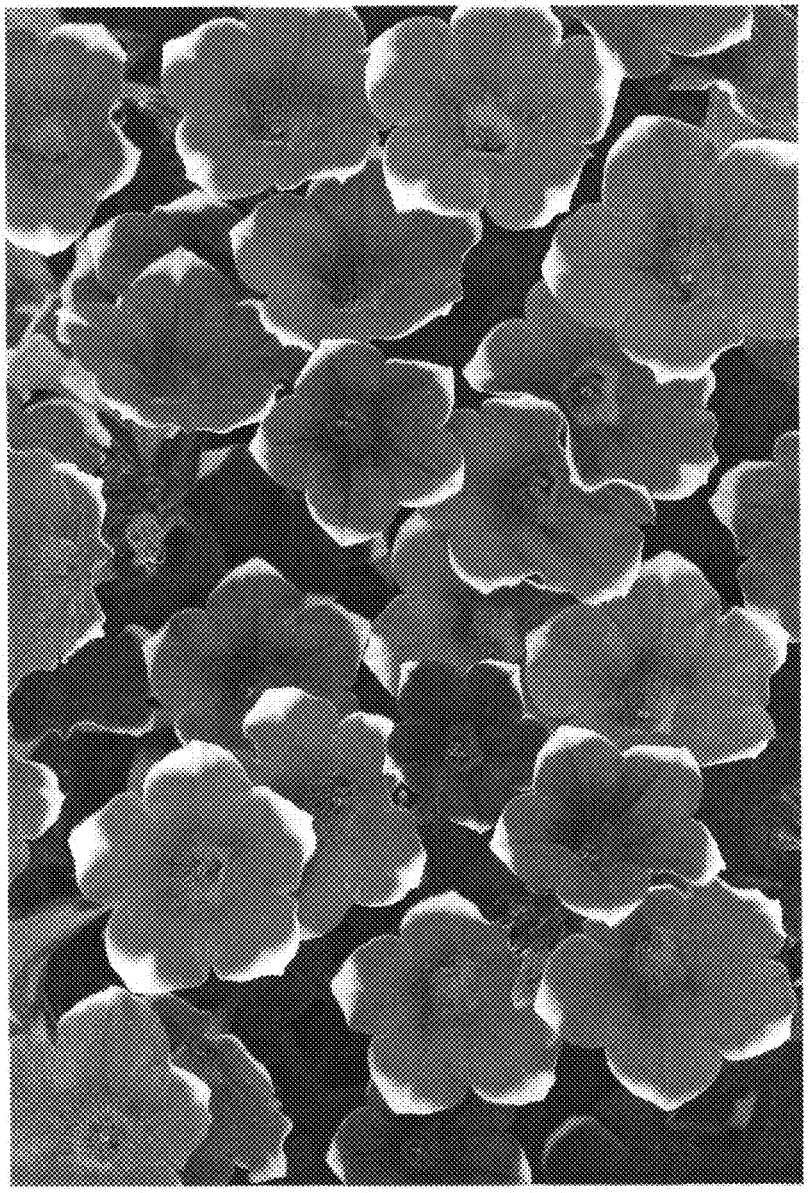

FIG. 2 illustrates in full color a close up of typical blooms of 'DCAS301'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DCAS301' plants grown in a greenhouse, in Moshav Mishmar Hashiva, Israel. The growing temperature ranged from 20° C. to 35° C. during the day and from 17° C. to 23° C. during the night. General light conditions are bright, normal sunlight. Measurements and numerical values represent averages of typical plant types.

Botanical classification: *Petunia sensu wijsman* 'DCAS301'.

PROPAGATION

Time to initiate roots: 10 to 14 days at approximately 20° C.
Root description: Fibrous.

PLANT

Age of plant described: Approximately 60 days from a rooted cutting.
Growth habit: Semi-trailing.
Pot size of plant described: 13 cm.
Height: To top of flowers: About 20 cm.
Plant spread: About 50 cm.
Growth rate: Strong.
Branching characteristics: Very branched.
Length of primary lateral branches: About 30 cm.
Diameter of lateral branches: About 0.3 cm.
Quantity of primary lateral branches: 8.
Characteristics of primary lateral branches:
- *Form*.—Cylindrical.
- *Diameter*.—About 0.3 cm.
- *Color*.—Green 143 A RHS.
- *Texture*.—Pubescent.
- *Strength*.—Strong, flexible.

Internode length: About 2 cm.

FOLIAGE

Leaf:
- *Arrangement*.—Opposite.
- *Quantity*.—Approximately 30 per branch.
- *Average length*.—5 cm.
- *Average width*.—2.5 cm.
- *Shape of blade*.—Elliptic.
- *Apex*.—Acute.
- *Base*.—Tapered.
- *Margin*.—Entire.
- *Texture of top surface*.—Velvety.
- *Texture of bottom surface*.—Pubescent.
- *Aspectl*.—90 degrees.
- *Color*.—Young foliage upper side: RHS Green 137 B. Young foliage under side: RHS Green 137 C. Mature foliage upper side: RHS Green 137 B. Mature foliage under side: RHS Green 137 C.
- *Venation*.—Type: Pinnate. Venation color upper side: RHS Green 137 C. Venation color under side: RHS Green 137 D.
- *Petiole*.—Length: About 0.6 cm. Diameter: About 0.2 cm. Color: RHS Green 137 B.
- *Texture*.—Velvety.

FLOWER

Natural flowering season: Spring, Summer and Autumn.
Days to flowering from rooted cutting: About 30 days.
Inflorescence and flower type and habit: Axillary, single flower, salverform shape, outward facing.
Rate of flower opening: 2 to 3 days from bud to fully opened flower.
Flower longevity on plant: 3 to 6 days.
Approximate quantity of flowers per plant: About 60.
Persistent or self-cleaning: Self-cleaning.
Bud:
- *Shape*.—Tubular.
- *Length*.—About 3.0 cm.
- *Diameter*.—About 0.5 cm.
- *Color*.—RHS Purple N77B.

Flower size:
- *Diameter*.—About 4 cm.
- *Flower tube length*.—About 2 cm.
- *Flower tube diameter at distal end*.—1.0 cm.
- *Flower tube diameter at proximal end*.—0.3 cm.

Petals:
- *Length from throat*.—About 1.5 cm.
- *Width*.—About 1.6 cm.

*Quantity*.—5.
*Texture*.—Velvety.
*Apex*.—Acute.
*Base*.—Tapered.
*Margin*.—Entire.

Color:
*When opening*.—Upper surface: RHS Purple N 79 C with a White Rim, RHS White NN155 D. Lower surface: RHS Purple 79 C.
*Fully opened*.—Upper surface: RHS Red-Purple 71 A with a White Rim, RHS White NN155 D. Lower surface: RHS Purple N 79 D. Flower throat (inside): RHS White N155A, streaked Violet N 88 B, becoming more densely streaked to nearly solid N88B at apex of slower tube. Flower throat, vein: RHS Violet N 88 A. Flower tube (outside): RHS Violet 85 C. Flower tube, vein: RHS Yellow-Green 151 C.
*Fading*.—Petals fading to: RHS Red-Purple 71 C.

Calyx/sepals:
*Quantity per flower*.—5.
*Shape*.—Linear.
*Length*.—About 1.0 cm.
*Width*.—About 0.1 cm.
*Apex*.—Rounded.
*Base*.—Fused.
*Margin*.—Entire.
*Texture*.—Velvety upper and lower surfaces. Color: Upper Surface: RHS Green 137 B. Lower Surface: RHS Green 137 C.

Peduncle:
*Length*.—About 2 cm.
*Diameter*.—About 0.1 cm.
*Color*.—RHS Green 137 B.
*Orientation*.—45 degrees.

Fragrance: None.

REPRODUCTIVE ORGANS

Stamens:
*Number*.—5.
*Filament length*.—About 1.5 cm.

Anthers:
*Length*.—About 0.1 cm.
*Shape*.—Rounded.
*Color*.—RHS Violet-Blue 98 B.
*Pollen*.—Color: RHS Violet-Blue 98 C. Quantity: Plenty.

Pistil:
*Number*.—1.
*Length*.—About 1.6 cm.
*Style*.—Length: About 1.9 cm. Color: RHS Yellow-Green 149 C.
*Stigma*.—Shape: Rounded. Color: RHS Green 144 D. Ovary Color: RHS Green 144 C.

OTHER CHARACTERISTICS

Seeds and fruits: About 40 brown, rounded seeds of about 0.5 mm diameter, per one brown, conical capsule. Size too small for accurate R.H.S. color.

Disease/pest resistance: Neither resistance nor susceptibility to the normal diseases and pest of *Petunia* have been observed. Typical well known diseases include: *Botrytis cineria, Fusarium, Pythium, Phytophthora,* and *Rhizoctonia* species. Typical well known pests include: Leaf miners, spider mites, thrips and possibly caterpillars.

Temperature tolerance: 5-40° C.

What is claimed is:

1. A new and distinct cultivar of *Petunia* plant named 'DCAS301' as herein illustrated and described.

* * * * *